United States Patent
Terasaki et al.

(10) Patent No.: US 9,354,238 B2
(45) Date of Patent: May 31, 2016

(54) COMPOSITIONS AND METHODS FOR THE DETECTION OF ANTIBODIES TO NATIVE HUMAN LEUKOCYTE ANTIGEN

(71) Applicant: ONE LAMBDA, INC., Canoga Park, CA (US)

(72) Inventors: Paul Terasaki, Los Angeles, CA (US); Adam Idica, Vista, CA (US); Chun-Tsan Deng, Los Angeles, CA (US)

(73) Assignee: ONE LAMBDA, INC., Canoga Park, CA (US)

( * ) Notice: Subject to any disclaimer, the term of this patent is extended or adjusted under 35 U.S.C. 154(b) by 0 days.

(21) Appl. No.: 14/581,375

(22) Filed: Dec. 23, 2014

(65) Prior Publication Data

US 2015/0111783 A1 Apr. 23, 2015

Related U.S. Application Data (62) Division of application No. 13/029,028, filed on Feb. 16, 2011, now Pat. No. 8,927,290.

(60) Provisional application No. 61/338,258, filed on Feb. 17, 2010.

(51) Int. Cl.
| | | |
|---|---|---|
| *G01N 33/532* | (2006.01) | |
| *G01N 33/564* | (2006.01) | |
| *G01N 33/566* | (2006.01) | |
| *G01N 33/68* | (2006.01) | |

(52) U.S. Cl.
CPC .......... *G01N 33/6854* (2013.01); *G01N 33/532* (2013.01); *G01N 33/564* (2013.01); *G01N 33/566* (2013.01); *G01N 2333/70539* (2013.01); *G01N 2800/24* (2013.01); *G01N 2800/245* (2013.01); *Y10T 436/25125* (2015.01); *Y10T 436/25375* (2015.01)

(58) Field of Classification Search
CPC ............ G01N 33/6854; G01N 33/532; G01N 33/564; G01N 33/566; G01N 2800/24; G01N 2800/245; G01N 2333/70539
See application file for complete search history.

(56) References Cited

U.S. PATENT DOCUMENTS

| | | | |
|---|---|---|---|
| 7,972,804 B2 * | 7/2011 | Lee et al. ..................... | 435/7.24 |
| 8,927,290 B2 * | 1/2015 | Idica et al. ..................... | 436/23 |
| 2009/0011437 A1 | 1/2009 | Lee et al. | |

FOREIGN PATENT DOCUMENTS

| | | |
|---|---|---|
| DE | 102004019803 A1 | 11/2005 |
| DE | 102004019803 A1 * | 11/2005 |
| EP | 1882700 A1 | 1/2008 |
| WO | WO-2004/029280 A2 | 4/2004 |
| WO | WO-2009/006312 A1 | 1/2009 |

OTHER PUBLICATIONS

Cai et al. Intact HLA Not β2m-free Heavy Chain-Specific HLA Class I Antibodies Are Predictive of Graft Failure, Transplantation 88: 226-230 (2009).*
Huang et al., Development of chymotrypsin clinical application, Shanghai Medicine, 26(10):462-4 (2005).
Third Office Action, Chinese Patent Application No. 201180010106.4, dated Feb. 16, 2015 (English translation).
Yu et al., Research on superspectrum beta-lactamase, China Medical Magazine, 86(9):641-4 (2006).
Zhang et al., Research on acetylcholinesterase molecular biology, Agricultural Chemicals, 45(1):8-11 (2006).
Cai et al., Intact HLA not beta2m-free heavy chain-specific HLA class I antibodies are predictive of graft failure, Transplantation, 88:226-30 (2009).
International Search Report and Written Opinion for PCT/US2011/025060, mailed May 18, 2011, 16 pgs.

* cited by examiner

*Primary Examiner* — Gail R Gabel
(74) *Attorney, Agent, or Firm* — Marshall, Gerstein & Borun LLP (57) ABSTRACT

Provided herein are compositions comprising native and denatured human leukocyte antigens (HLA) and methods of making said compositions. Also provided herein are methods and kits for the detection of antibodies to native HLAs.

10 Claims, 9 Drawing Sheets

COMPOSITIONS AND METHODS FOR THE DETECTION OF ANTIBODIES TO NATIVE HUMAN LEUKOCYTE ANTIGEN

1. CROSS REFERENCE TO RELATED APPLICATIONS

The present application is a divisional of U.S. patent application Ser. No. 13/029,028, now U.S. patent No. 8,927,290, filed Feb. 16, 2011 which claims the benefit of priority under 35 U.S.C. §119 of U.S. Provisional Application No. 61/338,258, the content of which are hereby incorporated by reference in their entirety.

2. FIELD OF THE INVENTION

The compositions and methods provided herein generally relate to compositions that are useful, for example, in the detection of antibodies to native human leukocyte antigen (HLA), and methods of their preparation.

3. BACKGROUND

Human leukocyte antigens (HLAs) can bind and display antigens on the surface of human cells to effector T cells. The two major classes of HLAs, class I and class II HLAs, present both foreign and native antigens. Class I HLAs can bind and present peptide antigens produced intracellularly, including viral and tumor specific proteins, to CD8+ effector T cells (e.g., cytotoxic T cells (CTLs)). In response to foreign antigens presented by class I HLA bearing cells, CD8+ effector T cells can destroy the cells presenting the foreign antigen. Class II HLAs can bind and present peptide antigens that originate extracellularly to CD4+ T cells (e.g., helper T cells). In response to foreign antigens presented by class II HLA bearing cells, CD4+ effector T cells can mount humoral immune responses. HLAs are thought to play a role in certain cancers and autoimmune disorders as well as graft rejection.

Antibodies to HLAs are usually produced by alloimmunization resulting from transfusions, pregnancies or transplants. They have also been found in nonalloimmunized individuals. Morales-Buenrostro et al., *Transplantation* 86: 1111-15 (2008). Antibodies to HLAs found in transplant recipients have been shown to be a cause of acute and chronic graft rejection. Thus, determining whether a recipient carries antibodies to HLAs of a donor can be important in determining the risk of graft rejection in a recipient.

To date, substrates linked to HLAs have been helpful in the detection of antibodies to HLAs. Samples from recipients are contacted with a substrate, and antibodies that bind to the substrate subsequently can be detected using conventional techniques. Conventional substrates, however, are typically linked to both native and denatured HLAs. Thus, these substrates are limited in their ability to distinguish between antibodies to native and denatured HLAs.

In some instances, antibodies to native HLAs, but not to denatured HLAs, are predictive of graft failure. Cai et al., *Transplantation* 88(2): 226-31 (2009). Therefore, there is a need for compositions and methods capable of detecting antibodies to native HLA without the interference of antibodies to denatured HLAs. Such compositions and methods can be used to prevent prospective donors from being excluded due to false positive signals, for example, when assays screening recipients for antibodies to donor HLAs detect, instead, antibodies to denatured HLAs.

4. SUMMARY

Provided herein are compositions and methods capable of, for example, the detection of antibodies to native HLAs. In a first aspect provided herein is a composition comprising native and denatured HLAs, wherein the native HLAs are present in substantial amounts. In some embodiments, at least 90% of the HLAs are native and at most 10% of the HLAs are denatured. In some embodiments, at least 95% of the HLAs are native and at most 5% of the HLAs are denatured. In some embodiments, at least 99% of the HLAs are native and at most 1% of the HLAs are denatured.

In some embodiments, the native and denatured HLAs are selected from the group consisting of class I HLAs, class II HLAs and combinations thereof. In some embodiments, the HLAs are class I HLAs. In some embodiments, the HLAs are class II HLAs. In some embodiments, the HLAs are a combination of class I and class II HLAs.

The native and denatured HLAs can be of the same allele or two or more different alleles. In some embodiments, at least 90% of the HLAs are of the same allele. In some embodiments, at least 95% of the HLAs are of the same allele. In other embodiments, at least 99% of the HLAs are of the same allele.

In some embodiments, the native and denatured HLAs are linked to a solid substrate. The HLAs can be linked to the solid substrate by any technique known to those of skill in the art. In some embodiments, the HLAs are directly linked to the solid substrate. In other embodiments, the HLAs are indirectly linked to the solid substrate.

The solid substrate can be made of any suitable material known to those of skill in the art. In some embodiments, the solid substrate comprises a material selected from the group consisting of silica, gold, latex, polystyrene, polyethylene, polysulfone, hydrogel, polyvinyl chloride, glass, and combinations thereof.

Further, the form of solid substrate can be any form deemed suitable by those of skill in the art. In some embodiments, the solid substrate is selected from the group consisting of a plurality of beads, a plurality of microbeads, a plurality of microparticles, a plurality of microspheres, a well, a membrane, a polymer, a filter, a microarray and combinations thereof. In some embodiments, the solid substrate is a plurality of microbeads.

In some embodiments, the solid substrate comprises a detectable label. In some embodiments, the detectable label comprises a fluorescent dye, a radioactive label, a magnetic label or a bar code. In certain embodiments, the detectable label is a fluorescent dye.

In another aspect provided herein are panels comprising a plurality of solid substrates, wherein each solid substrate of the plurality is linked to HLAs, wherein at least 90% of the HLAs linked are native and at most 10% of the HLAs are denatured, wherein at least 90% of the HLAs linked to a particular solid substrate of the plurality are of the same allele, and wherein each solid substrate of the plurality is linked to a different HLA with respect to the other solid substrates of the plurality. In some embodiments, the HLAs comprise HLAs selected from the group consisting of class I HLAs, class II HLAs and combinations thereof. In some embodiments, the plurality comprises 4 solid substrates, 8 solid substrates, 16 solid substrates, or 32 solid substrates.

In another aspect provided herein are methods for making a composition comprising at least 90% native HLAs and at most 10% denatured HLAs. The methods comprise: a) contacting a first composition comprising native and denatured HLAs with a serine protease, lipase, esterase, or amidase under conditions wherein the serine protease, lipase, esterase, or amidase cleaves the denatured HLAs; and b) neutralizing the serine protease, lipase, esterase or amidase to yield a resulting composition comprising at least 90% native HLAs and at most 10% denatured HLAs. In certain embodiments, the HLAs are suspended in solution. In certain embodiments, the HLAs are linked to one or more solid substrates. In particular embodiments, the HLAs are linked to a plurality of microbeads or microparticles.

In some embodiments of the methods, the HLAs are contacted with a serine protease. In particular embodiments, the serine protease is trypsin. In some embodiments, the HLAs are contacted with a lipase. In particular embodiments, the lipase is a phospholipase. In some embodiments, the HLAs are contacted with an esterase. In particular embodiments, the esterase is acetylcholine esterase. In other embodiments, the esterase is a thioesterase. In some embodiments, the HLAs are contacted with an amidase.

In another aspect provided herein is a method of screening for antibodies to native HLAs. This method comprises the steps of: a) contacting a sample with a composition comprising HLAs linked to a solid substrate, wherein at least 90% of the HLAs are native and at most 10% of the HLAs are denatured; and b) detecting binding of an antibody to the composition, wherein binding of an antibody to the composition is indicative of antibodies to native HLAs.

In some embodiments, the sample is a biological sample. In some embodiments, the sample is taken from a human subject. In some embodiments, the sample is a blood sample taken from a human subject.

Detection of binding of antibody to the composition can be performed by any technique known to those of skill the art. In some embodiments, the detection of antibody binding is performed using flow cytometry. In some embodiments, detection of antibody binding is performed using a secondary antibody. In particular embodiments, the secondary antibody comprises a label selected from the group consisting of a radioactive label, a fluorescent label, an enzymatic label, an avidin label, a biotin label and combinations thereof.

In another aspect provided herein are kits for the detection of antibodies to native HLA. These kits comprise: a) a composition comprising HLAs linked to a solid substrate, wherein at least 90% of the HLAs are native and at most 10% of the HLAs are denatured, and b) a reagent for detecting the binding of antibodies to the composition. In some embodiments, the reagent comprises a secondary antibody. In certain embodiments, the secondary antibody comprises a detectable label selected from the group consisting of a radioactive label, a fluorescent label, an enzymatic label, an avidin label, a biotin label and combinations thereof.

The compositions and methods provided herein advantageously allow for the detection of antibodies to native HLAs without the undesired detection of antibodies to denatured HLAs. Detection of antibodies that are specific for native HLAs is useful in certain instances, for example, when the presence of antibodies to native, but not denatured, HLAs is predictive of graft failure. Under these circumstances, the compositions and methods provided herein can help prevent prospective donors from being excluded due to false positive signals caused by the detection of antibodies to denatured HLAs in recipients.

6. DETAILED DESCRIPTION OF THE EMBODIMENTS

6.1 Definitions

As used herein, the terms "native," "native human leukocyte antigen," and "native HLA" refer to an HLA or fragment thereof that maintains the structural and antigenic property of the extracellular portion of an HLA in its native state.

As used herein, the terms "native class I human leukocyte antigen," and "native class I HLA" refer to a class I human leukocyte antigen or fragment thereof that maintains the structural and antigenic integrity of the extracellular portion of a class I HLA in its native state, including comprising a $\beta 2$ microglobulin domain noncovalently bound to a heavy chain or fragment thereof. In some embodiments, native class I HLAs are capable of binding to W6/32 and BIH antibodies (One Lambda, Inc.).

As used herein, the terms "native class II human leukocyte antigen," and "native class II HLA" refer to a class II human leukocyte antigen or fragment thereof that maintains the structural and antigenic integrity of the extracellular portion of a class II HLA in its native state, including comprising a heterodimer that comprises two glycosylated polypeptide chains noncovalently bound to each other. In some embodiments, native class II HLAs are capable of binding to HB-145 (directed to HLA-DP, HLA-DQ, HLA-DR) and HB-180 (directed to HLA-DQ and HLA DR) antibodies (American Type Cultural Collection (ATCC)).

As used herein, the terms "denatured," "denatured human leukocyte antigen," and "denatured HLA" refer to an HLA comprising an extracellular domain that is not in a native confirmation.

As used herein, the terms "denatured class I human leukocyte antigen," and "denatured class I HLA" refer to class I human leukocyte antigen or fragment thereof that lacks a $\beta 2$ microglobulin domain. In some embodiments, denatured class I HLAs are capable of binding to HC10 (One Lambda, Inc,) and HB296 antibodies (ATCC).

As used herein, the terms "denatured class II human leukocyte antigen" and "denatured class II HLA" refer to a class II human leukocyte antigen or fragment thereof that is in a monomeric confirmation. In some embodiments, denatured class II HLAs are capable of binding HB-298 (directed to HLA-DR $\alpha$ chain) antibody (ATCC).

As used herein, the term "solid substrate" refers to any solid substrate that is capable of binding HLAs and is compatible with the methods provided herein. Examples of solid substrates include a plurality of beads, a plurality of microbeads, a plurality of microparticles, a plurality of microspheres, a well, a membrane, a polymer, a filter, a microarray and combinations thereof.

As used herein, the term "same HLA allele" refers to two or more HLA molecules or fragments thereof that share similar structure and antigenic properties and are derived from the same HLA gene loci and alleles.

As used herein, the term "different HLA allele" refers to HLA molecules or fragments thereof that possess different structure and antigenic properties and are derived from different HLA gene loci and alleles.

6.2 Compositions for the Detection of Antibodies to Native HLA

Provided herein is a composition comprising at least 90% native HLAs and at most 10% denatured HLAs. In certain embodiments, the composition can be used for the detection of antibodies to native HLAs. Detection of antibodies to native HLAs can be useful, for example, in determining the likelihood of a graft rejection. In certain embodiments, the composition can also be useful in the development of HLA vaccines and effector T cell binding assays.

The composition can be made by any technique apparent to one of skill in the art, including the methods described herein. Each element of the composition is discussed in further detail below.

6.2.1. Native HLA

In some embodiments, the composition provided herein comprises at least 90% native HLAs and at most 10% denatured HLAs. In some embodiments, the HLAs are linked to a solid support. In other embodiments, the HLAs are in solution.

Native class I HLAs are 57 kDa glycoproteins that are present on most nucleated human cells. Native class I HLAs typically comprise a 45 kDa polypeptide heavy chain bound to a light chain that comprises a 12 kDa β2 microglobulin domain. In certain embodiments, the heavy chain is noncovalently bound to the light chain. The heavy chain typically comprises three a subunits, a transmembrane domain, and a cytoplasmic tail. The α1 and α2 subunits form a binding groove for peptide ligand binding. A denatured class I HLA, in contrast, lacks a β2 microglobulin domain.

The class I HLA heavy chain is encoded by one of three major genes (HLA-A, HLA-B and HLA-C) or one of three minor genes (HLA-E, HLA-F and HLA-G). Allelic variation within each of these gene loci helps contribute to the polymorphism exhibited by class I HLA. A particular class I HLA can be categorized by the gene locus and the particular allele from which the class I HLA is expressed. Exemplary class I HLA alleles are listed in Table 1 (HLA-A alleles), Table 2 (HLA-B alleles) and Table 3 (HLA-C alleles).

Native class II HLAs are polymorphic 61 kDa heterodimeric proteins that are present on the surface of specialized antigen presenting cells (e.g., B lymphocytes, dendritic cells, and macrophages). Class II HLAs are divided into three subclasses: HLA-DP, HLA-DQ and HLA-DR. A native class II HLA typically comprises an a chain and β chain bound to each other. In certain embodiments, the a chain and chain are noncovalently bound to each other. In contrast, denatured class II HLAs are monomeric proteins.

Each chain of a class II HLA comprises an extracellular domain, a transmembrane domain and a cytoplasmic tail. There are six major class II HLA genes (HLA-DPA1, HLA-PB1, HLA-DQA1, HLA-DQB1, HLA-DRA and HLADRB1), each gene encoding either an α or β chain. Similar to the class I HLA genes, each class II HLA gene comprises many alleles. Class I and class II HLAs can be made using any technique known to those of skill in the art including recombinant DNA techniques as described in Pei et al., *Transplantation* 75(1): 43-49 (2003).

In some embodiments, the composition comprises a substantial amount of native HLAs. In some embodiments, at least 90% of the HLAs are native and at most 10% of the HLAs are denatured. In some embodiments, at least 95% of the HLAs are native and at most 5% of the HLAs are denatured. In some embodiments, at least 99% of the HLAs are native and at most 1% of the HLAs are denatured. In some embodiments, at least 99.5% of the HLAs are native and at most 0.5% of the HLAs are denatured. Techniques for making these compositions are described below.

In some embodiments, the composition comprises HLAs selected from the group consisting of class I HLAs, class II HLAs and combinations thereof. In some embodiments, the composition comprises class I HLAs. In some embodiments, the composition comprises class II HLAs. In some embodiments, the composition comprises a combination of class I and class II HLAs.

The composition can comprise full length native HLAs or fragments thereof. In some embodiments, the composition comprises full length native class I HLAs, each class I HLA comprising a heavy chain noncovalently bound to a β2 microglobulin domain. In some embodiments, the composition comprises full length class II HLAs, each class II FILA comprising an α chain noncovalently bound to a β chain.

In some embodiments, each HLA comprises a modification such as an deletion, addition or amino acid substitution that does not disrupt the structural and antigenic integrity of the native HLA extracellular domain. In some embodiments, each HLA is a class I HLA that comprises an extracellular domain of a native class I HLA. In some embodiments, each HLA is a class I HLA that comprises an extracellular domain and a fragment of a transmembrane domain of a native class I HLA. In some embodiments, each HLA is a class I HLA that comprises an extracellular domain and a transmembrane domain of a native class I HLA. In some embodiments, each HLA is a class I HLA that comprises an extracellular domain, a transmembrane domain and a fragment of a cytoplasmic tail of a native class I HLA.

In some embodiments, each HLA is a class II HLA that comprises an extracellular domain of a native class II HLA. In some embodiments, each HLA is a class II HLA that comprises an extracellular domain and a fragment of a transmembrane domain of a native class II HLA. In some embodiments, each HLA is a class II HLA that comprises an extracellular domain and a transmembrane domain of a native class II HLA. In some embodiments, each HLA is a class II HLA that comprises an extracellular domain, a transmembrane domain and a fragment of a cytoplasmic tail of a native class II HLA.

The composition provided herein can comprise HLAs of the same allele or to two or more different alleles. HLAs that are of the same allele share the same structure and antigenic properties and are derived from the same HLA loci and alleles.

In some embodiments, at least 90% of the HLAs are of the same allele. In some embodiments, at least 95% of the HLAs are of the same allele. In other embodiments, at least 99% of the HLAs are of the same allele.

In some embodiments, at least 90% of the HLAs are of the same allele and comprise an HLA-A class I HLA. In some embodiments, at least 90% of the HLAs are of the same allele and comprise an HLA-A class I HLA that is listed in Table 1. In some embodiments, at least 90% of the HLAs are of the same allele and comprise an HLA-B class I HLA. In some embodiments. at least 90% of the HLAs are of the same allele and comprise an HLA-B class I HLA that is listed in Table 2.

In some embodiments, at least 90% of the HLAs are of the same allele and comprise an HLA-C class I HLA. In some embodiments, at least 90% of the HLAs are of the same allele and comprise an HLA-C class I HLA that is listed in Table 3.

In some embodiments. at least 90% of the HLAs are of the same allele and comprise an HLA-DP class II HLA. In some embodiments, at least 90% of the HLAs are of the same allele and comprise an HLA-DQ class II HLA. In some embodiments, at least 90% of the HLAs are of the same allele and comprise an HLA-DR class II HLA.

6.2.2. Solid Substrates

In certain embodiments, the HLAs provided herein are linked to a solid substrate. Native HLAs linked to the solid substrate allow the composition to bind antibodies to native HLAs. The bound antibodies to native HLAs can be detected using any technique known to those of skill in the art.

In certain embodiments, a substantial amount of the HLAs linked to the solid substrate are native. As used herein, a "substantial amount" can be any amount that allows for the binding and detection of antibodies to native HLAs without significant binding of antibodies specific for denatured HLAs. This amount can be expressed as a percentage of the total number of native HLAs to total number of HLAs linked to the solid substrate. In some embodiments, at least 75% of the HLAs are native. In some embodiments, at least 80% of the HLAs are native. In some embodiments, at least 85% of the HLAs are native. In some embodiments, at least 90% of the HLAs are native. In some embodiments, at least 95% of the HLAs are native. In some embodiments, at least 99% of the HLAs are native. In some embodiments, at least 99.5% of the HLAs are native.

HLAs can be linked to the solid substrate by any technique known to those of skill in the art. Further, HLAs can be directly or indirectly linked to the solid substrate. In some embodiments. HLAs are directly linked to the solid substrate. In some embodiments, HLAs are directly linked to the solid substrate by absorption, chemical coupling or by chemical linkage through a tail element added to the HLA. In certain embodiments. HLAs are directly linked to the substrate by passive absorption. Cantarero et al., *Anal. Biochem.*, 105: 373-382 (1980). In some embodiments, HLAs are indirectly linked to the solid substrate by a linking moiety. In some embodiments, the linking moiety is selected from the group consisting of an antibody, a lectin, a CD8 molecule, a CD4 molecule, a T cell receptor and fragments thereof. In some embodiments, the linking moiety is a bifunctional cross-linker. Useful bifunctional cross-linkers are known to those of skill in the art.

The solid substrate can be made of any material known to those of skill in the art that is able to link to HLAs. Well known materials for solid substrates include glass, polystyrene, polypropylene, polyethylene, dextran, nylon, amylases, natural and modified celluloses, polyacrylamides, polysulfone, hydrogel, polyvinyl and magnetite. In some embodiments, the solid substrate comprises a material selected from the group consisting of silica, gold, latex, polystyrene, polyethylene, polysulfone, hydrogel, polyvinyl chloride, glass, and combinations thereof.

Further, the solid substrate can have any structural configuration deemed suitable by those of skill in the art. Solid substrates can comprise a plurality of beads, a plurality of microbeads, a plurality of microparticles, a plurality of microspheres, a well, a membrane, a polymer, a filter, a microarray and combinations thereof.

In some embodiments, the solid substrate is a plurality of microbeads. Useful microbeads are commercially available from sources such as Luminex, Inc., Invitrogen Corp., Polysciences, Inc. and Bangs Laboratories, Inc. to name a few. In certain embodiments, the microbeads are 2 to 8 µm in diameter. In certain embodiments, the microbeads are 4 to 6 µm in diameter.

In some embodiments, the solid substrate is a plurality of microparticles. In some embodiments, the microparticles are nanocrystals or quantum dots.

The solid substrate can also comprise a detectable label or any other identifying characteristic that can allow for the identification, separation and classification of antibodies bound to the HLAs. For example, the substrate can be a plurality of microbeads, each labeled with a fluorophore that allows the microbeads to be sorted using flow cytometry. Detectable labels can include fluorescent dyes, radioactive labels, magnetic labels, bar codes and combinations thereof. In certain embodiments, the detectable label is a fluorescent dye. In certain embodiments, the detectable label is a radioactive label. In certain embodiments, the detectable label is a bar code. In certain embodiments, the substrate comprises a detectable label selected from the group consisting of a fluorescent dye, a radioactive label, a magnetic label, a bar code and combinations thereof.

6.3 Panels

In another aspect provided herein are panels comprising a plurality of solid substrates, wherein each solid substrate of the plurality is linked to HLAs, wherein at least 90% of the HLAs linked are native and at most 10% of the HLAs are denatured, wherein at least 90% of the HLAs linked to a particular solid substrate of the plurality are of the same allele, and wherein each solid substrate of the plurality is linked to a different HLA with respect to the other solid substrates of the plurality. The panels can be linked to any of the HLAs provided herein. Panels advantageously allow for the detection of multiple antibodies to one or more native class I HLAs at a time.

In some embodiments, the plurality comprises at least 2 or more solid substrates. In some embodiments, the plurality comprises at least 4 or more solid substrates. In some embodiments, the plurality comprises at least 8 or more solid substrates. In some embodiments, the plurality comprises at least 16 or more solid substrates. In some embodiments, the plurality comprises at least 32 or more solid substrates. In some embodiments, the plurality comprises at least 64 or more solid substrates. In some embodiments, the plurality comprises at least 128 or more solid substrates. In some embodiments, the plurality comprises at least 256 or more solid substrates.

In some embodiments, each solid substrate of the plurality is linked to HLA-A class I HLAs. In some embodiments, each solid substrate of the plurality is linked to HLA-B class I HLAs. In some embodiments, each solid substrate of the plurality is linked to HLA-C class I HLAs. In some embodiments, each solid substrate of the plurality is linked to any class I HLA selected from the class I HLAs found in Tables 1, 2, and 3 and combinations thereof.

In some embodiments, each solid substrate of the plurality is linked to HLA-DP class II HLAs. In some embodiments, each solid substrate of the plurality is linked to HLA-DQ class II HLAs. In some embodiments, each solid substrate of the plurality is to HLA-DR class II HLAs.

In some embodiments, the panel comprises a plurality of substrates linked to HLAs selected from the group consisting of HLA-A, HLA-B. HLA-C, HLA-DP, HLA-DQ, HLA-DR and combinations thereof.

In some embodiments, at least 90% of the HLAs linked to a particular solid substrate are of the same allele. In some embodiments, at least 95% of the HLAs linked to a particular solid substrate are of the same allele. In some embodiments, at least 99% of the HLAs linked to a particular solid substrate are of the same allele. In some embodiments, at least 99.5% of the HLAs linked to a particular solid substrate are of the same allele.

6.4 Methods for Making Compositions Useful for the Detection of Antibodies to Native HLAs In another aspect of the invention provided herein are methods for making compositions comprising at least 90% native human leukocyte antigens and at most 10% denatured human leukocyte antigens. In some embodiments, the method comprises: a) contacting a first composition comprising native and denatured HLAs with a serine protease, lipase, esterase, or amidase under conditions wherein the serine protease, lipase, esterase or amidase cleaves the denatured HLAs; and b) neutralizing the serine protease, lipase, esterase or amidase to yield a resulting composition comprising at least 90% native human leukocyte antigens and at most 10% denatured human leukocyte antigens. The methods can be used to make any of the compositions comprising at least 90% native HLAs and at most 10% denatured HLAs provided herein.

6.4.1. Composition of Native and Denatured HLAs

The HLAs of the first composition can comprise one or more classes of HLAs. In some embodiments, the HLAs comprise HLAs selected from the group consisting of class I HLAs, class II HLAs and combinations thereof. In some embodiments, the HLAs comprise class I HLAs. In some embodiments, the HLAs comprise class II HLAs. In some embodiments, the HLAs comprise a combination of class I and class II HLAs.

In some embodiments, the HLAs of the first composition can be in solution. In other embodiments, the HLAs are attached to a solid substrate.

In some embodiments, the HLAs of the first composition are suspended in solution. The HLAs can be suspended or solubilized in any solution deemed suitable to those of skill in the art. In certain embodiments, the solution is a buffer solution. In certain embodiments, the solution comprises additives that can help to prevent the nonspecific degradation of the HLAs but allow for specific cleavage of denatured HLAs. Examples of such additives include protease inhibitors, antimicrobial agents, metal chelators and reducing agents.

In some embodiments, the HLAs are in a solution comprising phosphate buffer solution (PBS). In some embodiments, the HLAs are in a solution comprising a metal chelator. In certain embodiments, the metal chelator is ethylenediaminetetraacetic acid (EDTA). In some embodiments, the HLAs are in a solution comprising an antimicrobial agent. In certain embodiments, the antimicrobial agent is sodium azide. In certain embodiments, the antimicrobial agent is thimerosal. In certain embodiments, the HLAs are in a solution comprising a reducing agent. In certain embodiments, the reducing agent is dithiothreitol (DTT). In certain embodiments, the reducing agent is 2-mercapthoethanol (2-ME).

Further, in some embodiments, the solution can comprise protease inhibitors that help to prevent nonspecific degradation of the native and denatured HLAs, but allow for cleavage of the denatured HLAs. In some embodiments, the solution comprises a protease inhibitor selected from the group consisting of an acid protease inhibitor, a thiol protease inhibitor, a metalloprotease inhibitor and combinations thereof. Examples of such inhibitors include pepstatin A (acid protease inhibitor), leupeptin (thiol protease inhibitor), antipain (thiol protease inhibitor), EDTA (metalloprotease inhibitor) and EGTA (metalloprotease inhibitor).

In some embodiments, the HLAs of the first composition are attached to a solid substrate. Solid substrates linked to native and denatured HLAs can be obtained using any technique known to those of skill in the art. Solid substrates linked to native and denatured HLAs can be obtained, for example, from a commercial source, include commercially available microbeads linked to either class I HLAs, class II HLAs or combinations thereof (e.g., FlowPRA class I and class II beads, LABScreen class I and class II PRA beads, LABScreen Mixed beads and LABScreen Single Antigen class I and class II beads (One Lambda, Inc.)). In other embodiments, solid substrates linked to native and denatured HLAs can be made by attaching recombinant native and denatured HLAs to a solid substrate. Recombinant native and denatured HLAs can be made and attached to solid substrates using any technique known to those of skill in the art, including, for example, techniques described in Pei et al., *Transplantation* 75(1): 43-49 (2003).

6.4.2. Cleavage of Denatured HLAs with a Serine Protease, Lipase, Esterase or Amidase In some embodiments, the methods comprise a step of contacting the first composition of native and denatured HLAs with a serine protease, lipase, esterase, or amidase under conditions wherein the serine protease, lipase, esterase or amidase cleaves the denatured HLAs.

Any serine protease, lipase, esterase or amidase known to those of skill in the art to cleave denatured HLAs can be contacted with the substrate. Ideally, the serine protease, lipase, esterase or amidase selectively cleaves denatured HLAs but leaves native HLAs intact. Further, the ability of a particular serine protease, lipase, esterase or amidase to selectively cleave denatured HLAs can vary with the temperature and duration of time the HLAs are contacted with the particular serine protease, lipase, esterase or amidase. One of skill in the art will be able to determine what the appropriate conditions can be for a particular protease, lipase, esterase or amidase to cleave denatured HLAs of a particular class.

In some embodiments of the methods, the HLAs are contacted with a serine protease that is capable of selectively cleaving denatured HLAs while leaving native HLAs intact. In particular embodiments, the HLAs are contacted with a serine protease from the trypsin-like clan, which includes trypsin, chymotrypsin, and elastase. In particular embodiments, the serine protease is trypsin. In particular embodiments, the serine protease is chymotrypsin. In particular embodiments, the serine protease is elastase. In other embodiments, the serine protease is subtilisin.

In some embodiments, the HLAs are contacted with a lipase that is capable of selectively cleaving denatured HLAs in the first composition while leaving native HLAs intact. In particular embodiments, the lipase is a phospholipase. In particular embodiments, the phospholipase is selected from the group consisting of phospholipase A, phospholipase B, phospholipase C and phospholipase D.

In some embodiments, the HLAs are contacted with an esterase that is capable of selectively cleaving denatured HLAs in the first composition while leaving native HLA intact. In particular embodiments, the esterase is acetylcholine esterase. In other embodiments, the esterase is a thioesterase. In particular embodiments, the thioesterase is selected from the group consisting of acetyl-coA hydrolase, palmitoyl-coA hydrolase, succinyl-coA hydrolase and acyl-coA hydrolase.

In some embodiments, the HLAs are contacted with an amidase that is capable of selectively cleaving denatured HLAs while leaving native HLAs intact. In some embodiments, the amidase is peptide amidase.

6.4.3. Neutralization of the Serine Protease, Lipase, Esterase or Amidase

After cleavage of denatured HLAs by protease, lipase, esterase or amidase, the enzymatic activity of the protease, lipase, esterase or amidase is neutralized. Neutralization of a particular protease, lipase, esterase or amidase can be performed using any technique known to those of skill in the art. For example, neutralization can be achieved by contacting a particular protease, lipase, esterase or amidase with a reagent comprising an inhibitor of said protease, lipase. esterase or amidase.

In some embodiments, neutralization is achieved by contacting a protease with a reagent comprising one or more protease inhibitors. In some embodiments, the protease inhibitor is a serine protease inhibitor. In particular embodiments, the serine protease inhibitor is a trypsin inhibitor. In particular embodiments, the trypsin inhibitor is aprotinin. In particular embodiments, the trypsin inhibitor is benzamidine. In particular embodiments. the trypsin inhibitor is phenylmethylsufonyl fluoride (PMSF). In particular embodiments, the trypsin inhibitor is Trypsin Neutralization Solution (Lonza, CC-5002). In particular embodiments, the serine protease inhibitor is a chymotrypsin inhibitor. In particular embodiments, the chymotrypsin inhibitor is chymotrypsin inhibitor 2. In particular embodiments, the serine protease inhibitor is an elastase inhibitor. In some embodiments, the elastase inhibitor is alpha 1-antitrypsin. In certain embodiments, the serine protease inhibitor is a subtilisin inhibitor. In certain embodiments, the subtilisin inhibitor is *Streptomyces* subtilisin inhibitor.

In some embodiments, neutralization is achieved by contacting a lipase with one or more lipase inhibitors. In certain embodiments, the lipase inhibitor is lipistatin. In some embodiments, neutralization is achieved by contacting an esterase with one or more esterase inhibitors. In some embodiments, the esterase inhibitor is an acetylcholinesterase inhibitor. In some embodiments, the acetylcholineserase inhibitor is an organophosphate or a carbamate. In some embodiments, the esterase inhibitor is a thioesterase inhibitor. In some embodiments, the thioesterase inhibitor is 5-(furan-2-ylmethylene) pyrimidine-2,4,6-trione. In some embodiments, neutralization is achieved by contacting an amidase with one or more amidase inhibitors. In some embodiments, the amidase inhibitor is a nitrile. In some embodiments, the nitrile is bis-p-nitrophenyl phosphate.

6.5 Methods for the Detection of Antibodies to Native HLAs

In another aspect provided herein are methods for the detection of antibodies to native HLAs. Detection of antibodies to native HLAs can be useful, for example, in the context of tissue or organ grafting, where detection of antibodies against donor native HLAs can be helpful in determining the risk of graft rejection.

In certain embodiments, these methods comprise the steps of: a) contacting a sample with a composition comprising HLAs linked to a solid substrate, wherein at least 90% of the HLAs are native and at most 10% of the HLAs are denatured; and b) detecting binding of an antibody to the composition, wherein binding of an antibody to the solid substrate is indicative of the presence of antibodies specific for native HLAs in the sample. The composition can comprise any of the compositions comprising HLAs linked to a solid substrate, wherein at least 90% of the HLAs are native and at most 10% of the HLAs are denatured provided herein.

In certain embodiments, at least 90% of the HLAs linked to the solid substrate are of the same allele. In certain embodiments, at least 95% of the HLAs linked to the solid substrate are of the same allele. In certain embodiments, at least 99% of the HLAs linked to the solid substrate are of the same allele. In certain embodiments, at least 99.5% of the HLAs linked to the solid substrate are of the same allele.

In certain embodiments, the HLAs are selected from the group consisting of class I HLAs, class II HLAs and combinations thereof. In certain embodiments, the HLAs are class I HLAs. In certain embodiments, the HLAs are class II HLAs. In certain embodiments, the HLAs are a combination of class I and class II HLAs.

In certain embodiments, the composition comprises a plurality of said solid substrates, wherein at least 90% of the HLAs linked to a particular solid substrate of the plurality are of the same allele and each solid substrate of the plurality is linked to different HLA alleles with respect to the other solid substrate of the plurality. In certain embodiments, the plurality comprises 4 or more solid substrates. In certain embodiments, the plurality comprises 8 or more solid substrates. In certain embodiments, the plurality comprises 16 or more solid substrates. In certain embodiments, the plurality comprises 32 or more solid substrates.

Any useful sample known to those of skill in the art can be used, including biological samples. Exemplary useful biological samples include whole blood, blood derivatives, red blood cell concentrates, plasma, serum, fresh frozen plasma, whole blood derived platelet concentrates, globulin, cryoprecpitate, cerebrospinal fluid, tissues and cells such as epithelial cells, such as those collected from the buccal cavity, stem cells, leukocytes, neutrophils and granulocytes.

A sample can be obtained from a human donor of a tissue, cell or organ transplantation or the intended recipient of said tissue, cell or organ transplantation. In some embodiments, the sample is obtained from a human donor of a kidney, liver or heart transplantation. In some embodiments, the sample is obtained from the tissue, cells or organ intended for transplantation in a human recipient. In particular embodiments, the sample is obtained from a kidney, liver or heart intended from transplantation in a human recipient. In other embodiments, the sample is obtained from a human donor or recipient of a blood transfusion. In other embodiments, the sample is obtained from blood or blood derivatives intended for transfusion in a recipient. In certain embodiments, the sample is obtained from a human donor or recipient of a bone marrow transplantation.

Any system capable of detecting the binding of antibody to substrate known to those of skill in the art can be used to detect binding of an antibody. For example, detection of binding of antibodies to native HLAs can be performed using secondary antibodies conjugated to a detectable label such as a radioactive label, a fluorescent label, an enzymatic label, an avidin label, a biotin label, or combinations thereof. Further, substrates comprising detectable labels such as those described herein allow for multiplexed detection and classification of bound antibodies to native HLAs.

In particular embodiments, detection of antibody binding is performed using an immunosorbent sandwich assay such as an enzyme linked immunosorbent assay (ELISA) assay. Immunosorbent sandwich assays can be particular useful when the solid substrate used is a microtiter plate well. For membrane or filter solid substrates, detection of antibody binding can be performed using immunoblotting techniques. In other embodiments, detection of antibody binding is performed using flow cytometry.

6.6 Kits

In another aspect provided herein, are kits for the detection of antibodies to native HLAs. In certain embodiments, the kits comprise a) a composition comprising HLAs linked to a solid substrate, wherein at least 90% of the HLAs are native and at most 10% of the HLAs are denatured, and b) a reagent for the detection of binding of antibody to the composition. The composition can comprise any of the compositions comprising HLAs linked to a solid substrate, wherein at least 90% of the HLAs are native and at most 10% of the HLAs are denatured provided herein.

In certain embodiments, the composition comprises a plurality of said solid substrates, wherein at least 90% of the HLAs linked to a particular solid substrate of the plurality are of the same allele and each solid substrate of the plurality is linked to different HLA alleles with respect to the other solid substrate of the plurality. In certain embodiments, the plurality comprises 4 or more solid substrates. In certain embodiments, the plurality comprises 8 or more solid substrates. In certain embodiments, the plurality comprises 16 or more solid substrates. In certain embodiments, the plurality comprises 32 or more solid substrates.

Any reagent useful for detection of antibody binding known to those of skill in the art can be used. Secondary antibodies, for example, can be useful for the detection of antibody binding in assays such as Western blots, immunoblots, flow cytometry, ELISAs and radioimmunoassay (RIAs). In some embodiments, the reagent comprises a secondary antibody. In certain embodiments, the secondary antibody is an anti-human IgG antibody.

In some embodiments, the reagent comprises a secondary antibody comprising a detectable label. In certain embodiments, the kit comprises a detectable label selected from the group consisting of a radioactive label, a fluorescent label, an enzymatic label, an avidin label, a biotin label. and combinations thereof.

In some embodiments, the kits can further comprise wash buffers, control buffers, gels, loading buffers, molecular weight markers, plates comprising a plurality of wells and positive and negative control samples.

The following non-limiting examples illustrate certain embodiments described above.

7. EXAMPLES

The following examples are presented to further describe aspects of the invention. Example 1 describes a preparation of native class I HLA microbeads. Example 2 describes an assay method used to identify the types of class I HLAs on the native class I HLA microbeads. Example 3 provides analysis results to show the purity of the native class I HLA microbeads. Example 4 presents antibody reactivity results of the native class I HLA microbeads. In these examples, commercially available LABScreen products from One Lambda, Inc. are used and are identified by their catalogue numbers.

7.1 Example 1

Preparation of Microbeads Linked to Native Class I HLAs

The present example provides an exemplary preparation of microbeads linked to native class I HLAs ("native class I HLA microbeads"). LABScreen Single Antigen Beads (LSAB), specifically, LABScreen® Single Antigen HLA Class I—Combi (Catalogue ID: LS1A04), were obtained from One Lambda, Inc. Without treatment, LSAB contain both native and denatured class HLAs bound to the beads surfaces.

Figure 1A:
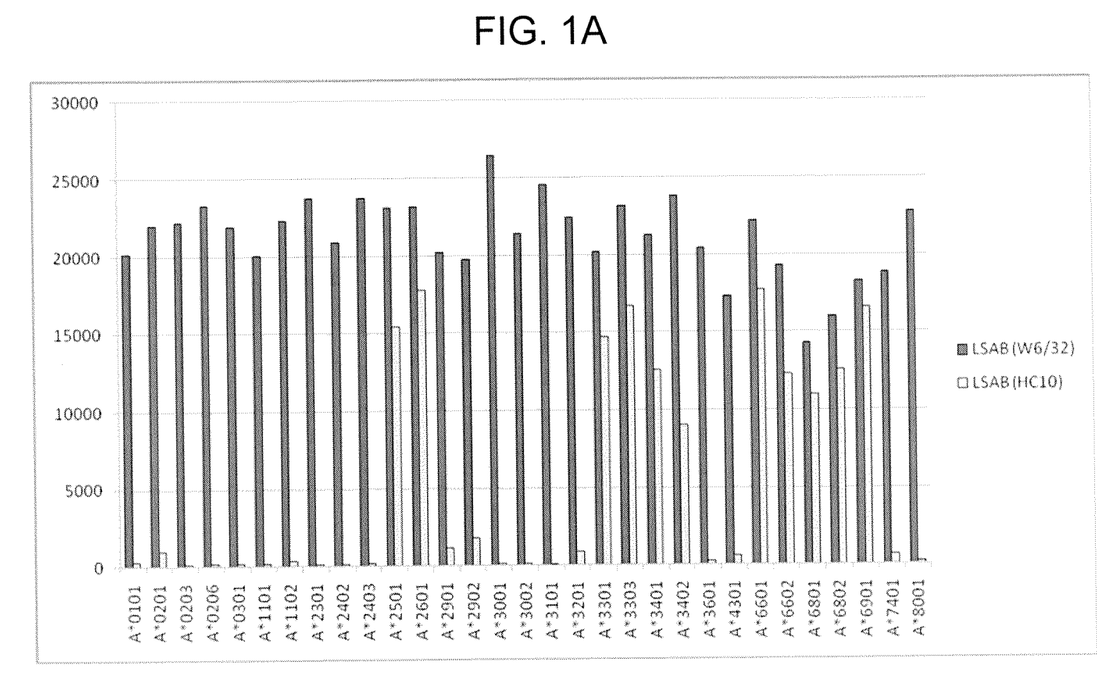
FIGS. 1A-1C provide graphs depicting the reactivity of an antibody specific for native class I HLA (W6/32) and denatured class I HLA (HC10) with LABScreen Single Antigen Beads (LSAB) for A-locus (FIG. 1A), B-locus (FIG. 1B) and C-locus (FIG. 1C) class I HLAs. They demonstrate the reactivity of both W6/32 and HC10 with LSAB.
Figure 1B:
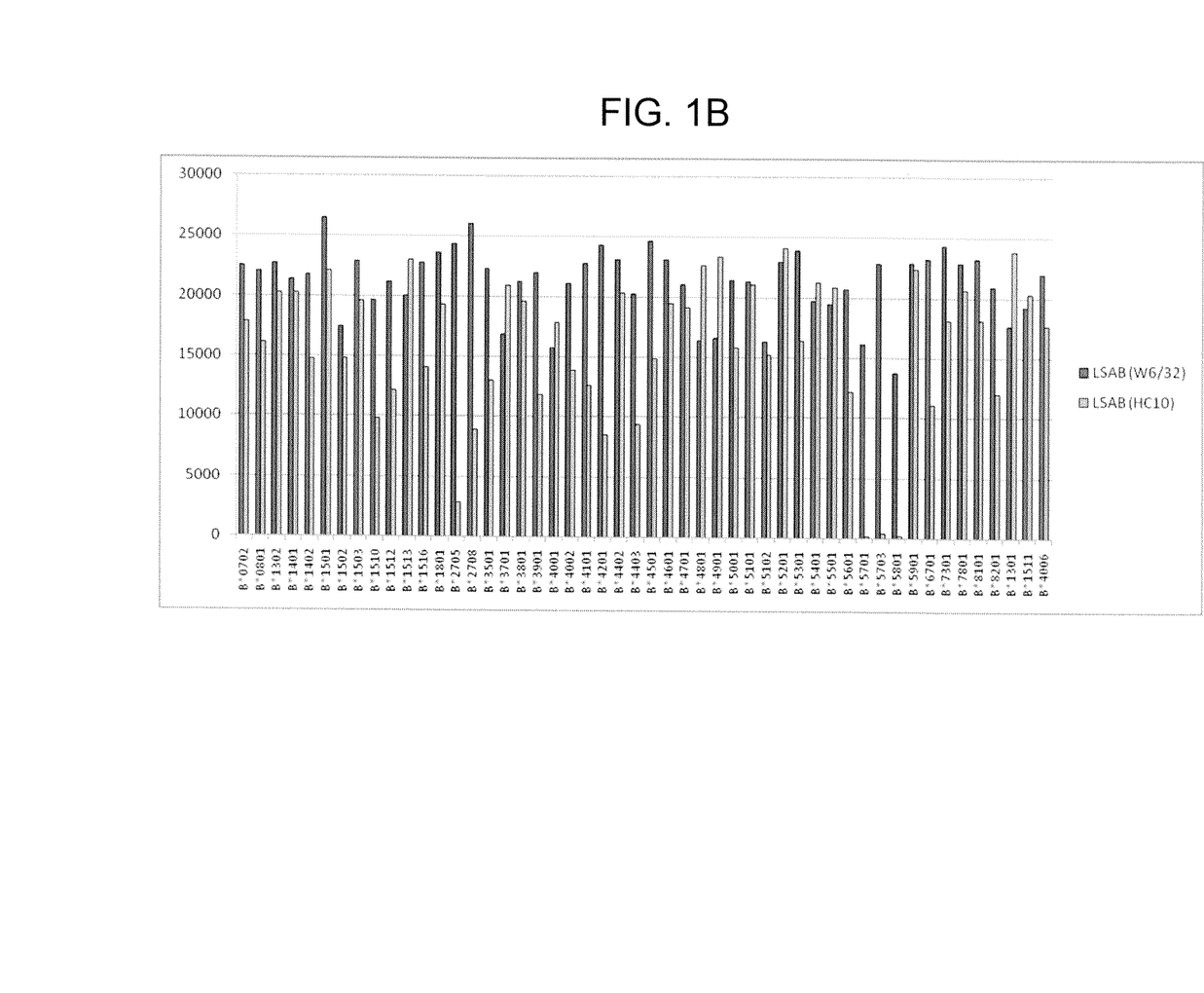
Figure 1C:
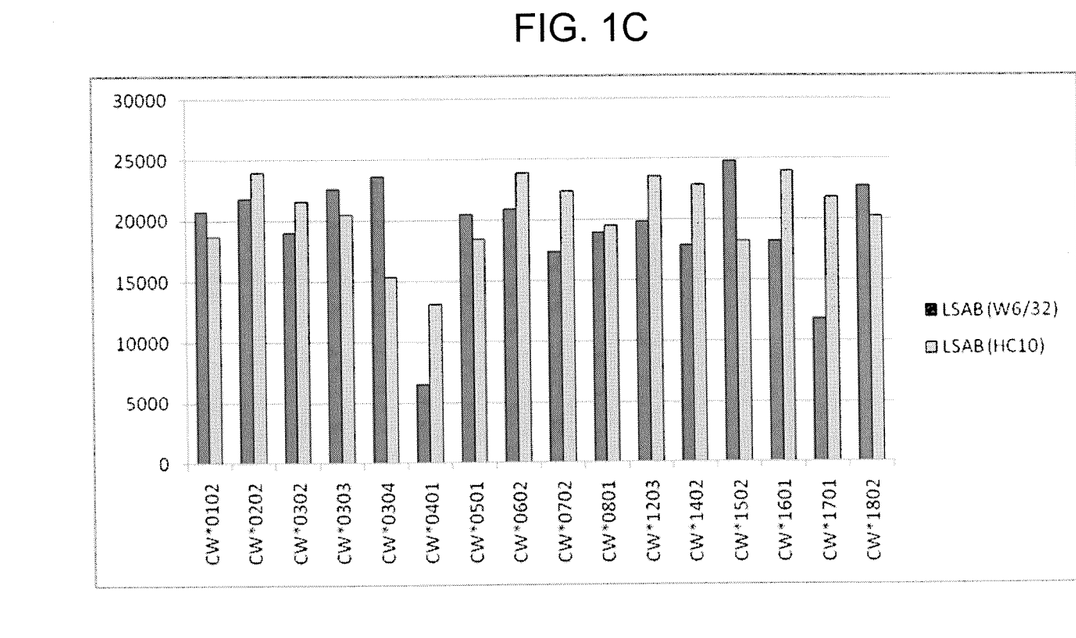

FIGS 1A-1C show the reactivity of W6/32 and HC10 with LSAB. Monoclonal antibody W6/32 specifically binds to native class I HLA. Monoclonal antibody HC10 specifically binds to denatured class I HLA. FIGS. 1A-1C depict median fluorescence intensity (MFI) with respect to specificities for A-locus (FIG. 1A), B-locus (FIG. 1B) and C-locus (FIG. 1C) class I HLA alleles. The level of MEI of the detection antibody corresponds to the level of antibody binding to either native or denatured class I HLA. These figures show that LSAB are reactive to both W6/32 and HC10 monoclonal antibodies.

To prepare the native class I HLA microbeads, denatured class I HLAs on the LSAB were subjected to selective proteolytic digestion with trypsin, a serine protease. Trypsin was purchased in lyophilized form from Worthington Biochemical Corporation of Lakewood, N.J. (Catalogue code TRL, Catalogue number LS00372).

The trypsin was reconstituted in 1×phosphate buffered saline (PBS), purchased from Irvine Scientific of Santa Ana. Calif., to working concentrations from about 0.00004% to about 0.04% weight/volume. The native class I HLA microbeads were exposed to Trypsin solution for about 30 minutes at about 37 degrees C.

The trypsin solution was then neutralized using Trypsin Neutralizing Solution (TNS) purchased from Lonza Walkersville, Inc. of Walkersville, Md. (Catalogue number CC-5002). Stock TNS was added at about 2:1 by volume after the about 30 minute digestion with trypsin. In other instances neutralization was accomplished by rapid dilution (about 1:2) using a mixture containing 1×PBS, about 0.1% bovine serum albumin (BSA).

Next, the microbeads were centrifuged at about 10,000 g for about two minutes and washed two times with about 1 mL of 1×LABScreen® wash buffer (Catalogue number LSPW ABUF) The microbeads were subsequently incubated overnight in about 2% BSA at about 4° C. Then the microbeads were washed three times with about 1 mL of LABScreen® wash buffer.

7.2 Example 2

Assays of Native Class I HLA Microbeads

This example demonstrates the high purity of exemplary microbeads prepared according to the methods described herein. To confirm that proteolytic digestion removed denatured class I HLAs, a panel of microbeads prepared according to Example 1 was incubated with either W6/32 or HC10 to detect native class I HLAs or denatured class I HLAs respectively.

About 1 μl of antibody diluted in about 100 μl of about 1×PBS were incubated with the native class I HLA microbeads for about 30 minutes at room temperature on a shaker. The microbeads were then washed three times with about 1 mL of LABScreen® wash and then incubated with about 100 μl of Phycoerythrin-conjugated (PE-conjugated) goat anti-mouse secondary antibody for about 30 minutes at room temperature on a shaker. Next, the microbeads were washed three times and analyzed by a Luminex flow machine.

Figure 2A:
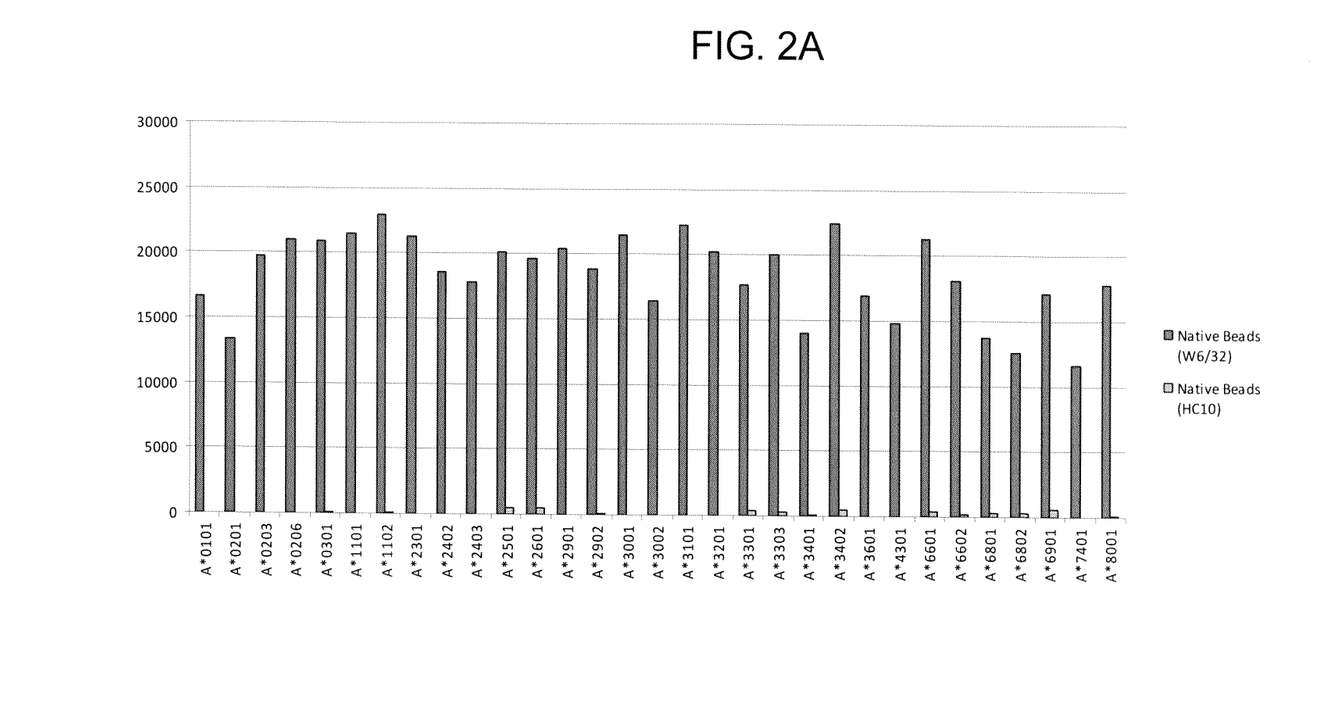
FIGS. 2A-2C provide graphs depicting the reactivity of W6/32 and HC10 with compositions ("native beads") for A-locus (FIG. 2A). B-locus (FIG. 2B) and C-locus (FIG. 2C) class I HLAs. The substrates used in these studies are microbeads. These graphs demonstrate the low reactivity of HC10 with compositions compared to LSAB.
Figure 2B:
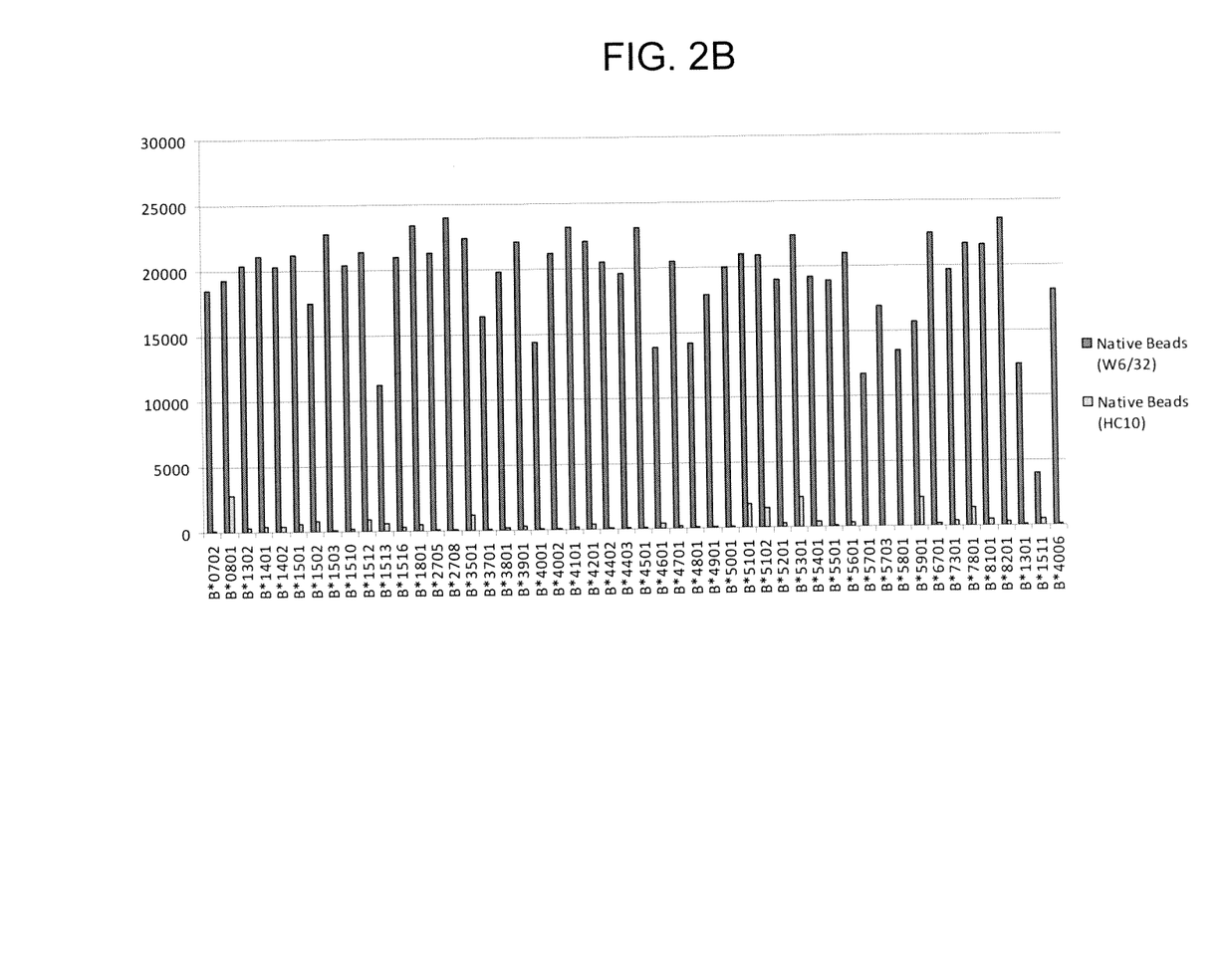
Figure 2C:
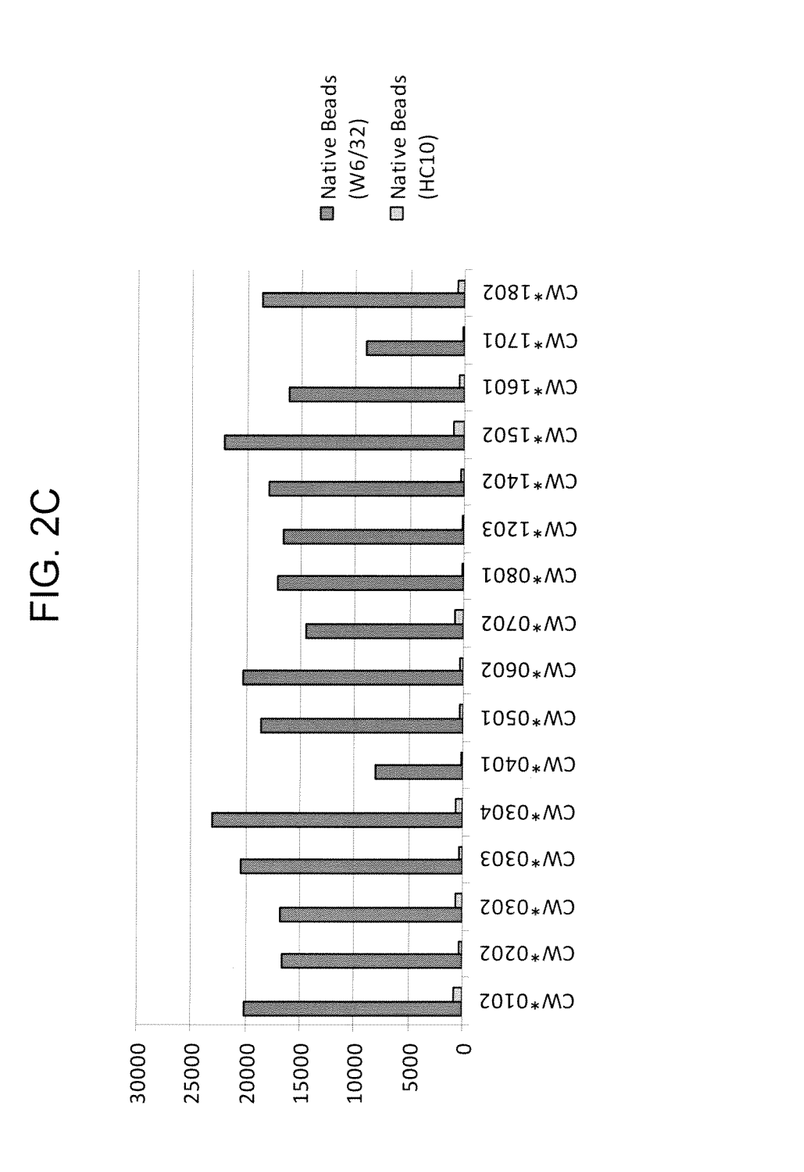

FIGS. 2A-2C provide the reactivity, of W6/32 (specific for native class I HLA) and HC10 (specific for denatured class I HLA) with the microbeads. The Y-axes represent the MFI and the X-axes represent specificities for A-locus (FIG. 2A, B-locus (FIG. 2B), and C-locus (FIG. 2C) class I HLA alleles. Raw data from the Luminex flow machine was normalized to remove non-specific or background signal by subtracting a sample negative control bead MFI from the MFI of all specificities in the bead panel. All normalized values over 1,000 MFI were considered positive. These figures show that the native class I HLA microbeads have low reactivity with HC10, indicating a low percentage of denatured class I HLAs remained on the native class I HLA microbeads.

7.3 Example 3

Purity of Native Class I HLA Microbeads

This example provides the purity of several exemplary samples of native class I HLA microbeads prepared according to the methods described herein. Tables 1-3 below show the percentage of denatured class I HLA remaining on microbeads made in accordance with the preparation procedure provided in Example 1 above and assayed in accordance with the procedure provided in Example 2 above. The percentage of denatured class I HLA was calculated according to the formula: [HC10 MFI/(HC10 MFI+W6/32 MFI)]*100. Data was taken from 98 samples (5 batches) of microbeads.

Table 1 below is data from native class I HLA microbead samples for specificities of A-locus class I HLA alleles. The data show the average percentage of denatured class I HLA of 0.81% with a standard deviation of 0.97%.

TABLE 1

Percentage of Denatured HLA on
Native Class I HLA Microbeads (A-Locus)

| Sample ID | % denatured class I HLA |
|---|---|
| A*0101 | 0.14 |
| A*0201 | 0.1 |
| A*0203 | 0.08 |
| A*0206 | 0.1 |
| A*0301 | 0.39 |
| A*1101 | 0.19 |
| A*1102 | 0.21 |
| A*2301 | 0.15 |
| A*2402 | 0.19 |
| A*2403 | 0.2 |
| A*2501 | 2.52 |
| A*2601 | 2.34 |
| A*2901 | 0.17 |
| A*2902 | 0.27 |
| A*3001 | 0.14 |
| A*3002 | 0.17 |
| A*3101 | 0.07 |
| A*3201 | 0.16 |
| A*3301 | 2.13 |
| A*3303 | 1.29 |
| A*3401 | 0.81 |
| A*3402 | 1.95 |
| A*3601 | 0.17 |
| A*4301 | 0.13 |
| A*6601 | 1.97 |
| A*6602 | 0.9 |
| A*6801 | 2.28 |
| A*6802 | 2.42 |
| A*6901 | 3.11 |
| A*7401 | 0.17 |
| A*8001 | 0.28 |

Table 2 below is data from microbeads samples for specificities of B-locus class I HLA alleles. The data show the average percentage of denatured class I HLA of 3.53% with a standard deviation of 3.86%.

TABLE 2

Percentage of Denatured HLA on
Native Class I HLA Microbeads (B-Locus)

| Sample ID | % denatured class I HLA |
|---|---|
| B*0702 | 1.02 |
| B*0801 | 12.81 |
| B*1302 | 1.13 |
| B*1401 | 6.64 |
| B*1402 | 3.67 |
| B*1501 | 4.98 |
| B*1502 | 4.34 |
| B*1503 | 0.68 |
| B*1510 | 2.4 |
| B*1512 | 1.58 |
| B*1513 | 8.92 |
| B*1516 | 5.16 |
| B*1801 | 1.41 |
| B*2705 | 0.54 |
| B*2708 | 0.75 |
| B*3501 | 4.6 |
| B*3701 | 0.29 |
| B*3801 | 4.4 |
| B*3901 | 2.1 |
| B*4001 | 0.91 |
| B*4002 | 0.6 |
| B*4101 | 1.26 |
| B*4201 | 2.2 |
| B*4402 | 0.31 |
| B*4403 | 0.3 |
| B*4501 | 0.58 |
| B*4601 | 2.96 |
| B*4701 | 1.62 |
| B*4801 | 4.14 |
| B*4901 | 0.56 |
| B*5001 | 0.76 |
| B*5101 | 5.59 |
| B*5102 | 7.05 |
| B*5201 | 1.62 |
| B*5301 | 10.37 |
| B*5401 | 2.93 |
| B*5501 | 2.16 |
| B*5601 | 1.83 |
| B*5701 | 6.69 |
| B*5703 | 0.16 |
| B*5801 | 18.45 |
| B*5901 | 12.12 |
| B*6701 | 1.06 |
| B*7301 | 2.23 |
| B*7801 | 4.23 |
| B*8101 | 2.4 |
| B*8201 | 1.62 |

TABLE 2-continued

Percentage of Denatured HLA on
Native Class I HLA Microbeads (B-Locus)

| Sample ID | % denatured class I HLA |
|---|---|
| B*1301 | 0.78 |
| B*1511 | 10.45 |
| B*4006 | 1.07 |

Table 3 below is data from microbeads samples for specificities of C-locus class I HLA alleles. The data show the average percentage of denatured class I HLA of 2.60% with a standard deviation of 1.24%.

TABLE 3

Percentage of Denatured HLA on
Native Class I HLA Microbeads (C-Locus)

| Sample ID | % denatured class I HLA |
|---|---|
| CW*0102 | 3.71 |
| CW*0202 | 2.22 |
| CW*0302 | 3.71 |
| CW*0303 | 1.43 |
| CW*0304 | 2.52 |
| CW*0401 | 2.01 |
| CW*0501 | 1.56 |
| CW*0602 | 1.88 |
| CW*0702 | 5.42 |
| CW*0801 | 1.28 |
| CW*1203 | 1.24 |
| CW*1402 | 1.67 |
| CW*1502 | 4.52 |
| CW*1601 | 2.99 |
| CW*1701 | 2.15 |
| CW*1802 | 3.33 |

Overall results for Tables 1-3 show an average percentage of denatured class I HLA of 2.51% with a standard deviation of 3.10% on the five batches of native class I HLA microbeads. These results demonstrate that native class I HLA microbeads can be made with high purity according to the present methods.

7.4 Example 4

Reactivity of Native Class I HLA Microbeads

Figure 3A:
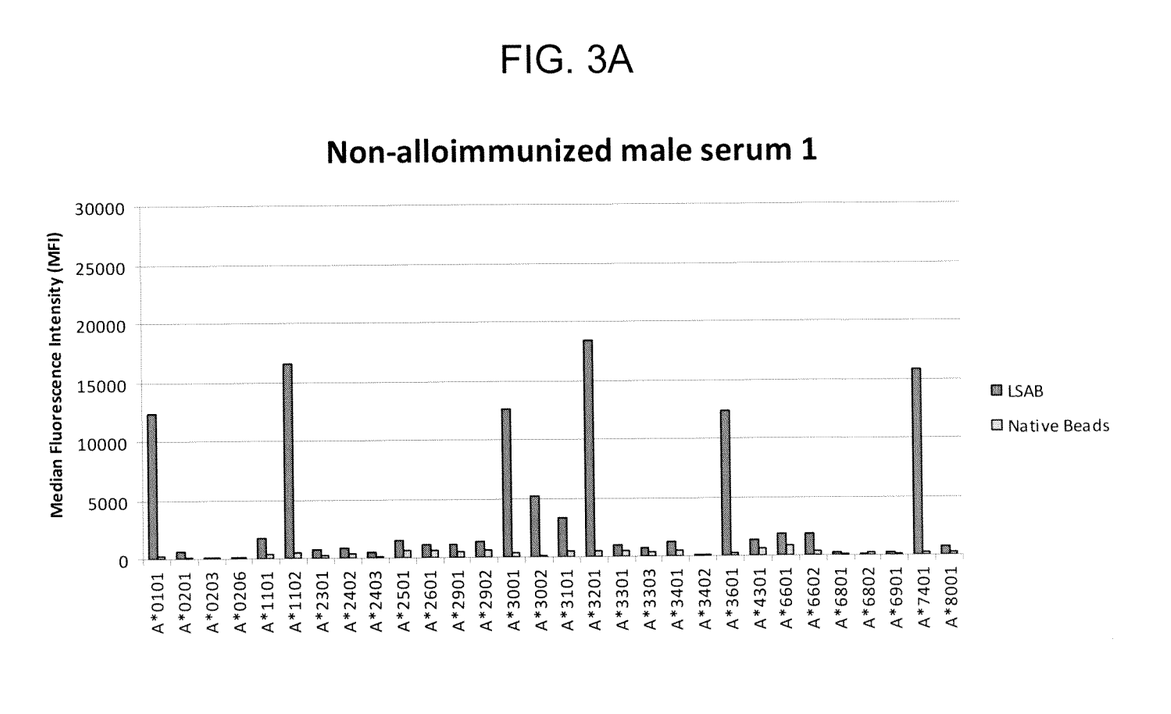
FIGS. 3A-3C provide graphs depicting the reactivity of three non-alloimmunized male sera with LSAB and compositions ("native beads") for A-locus (FIG. 3A), B-locus (FIG. 3B), and C-locus (FIG. 3C) HLA alleles. The substrates used in these studies are microbeads. These graphs demonstrate the improved accuracy of compositions compared to LSAB.
Figure 3B:
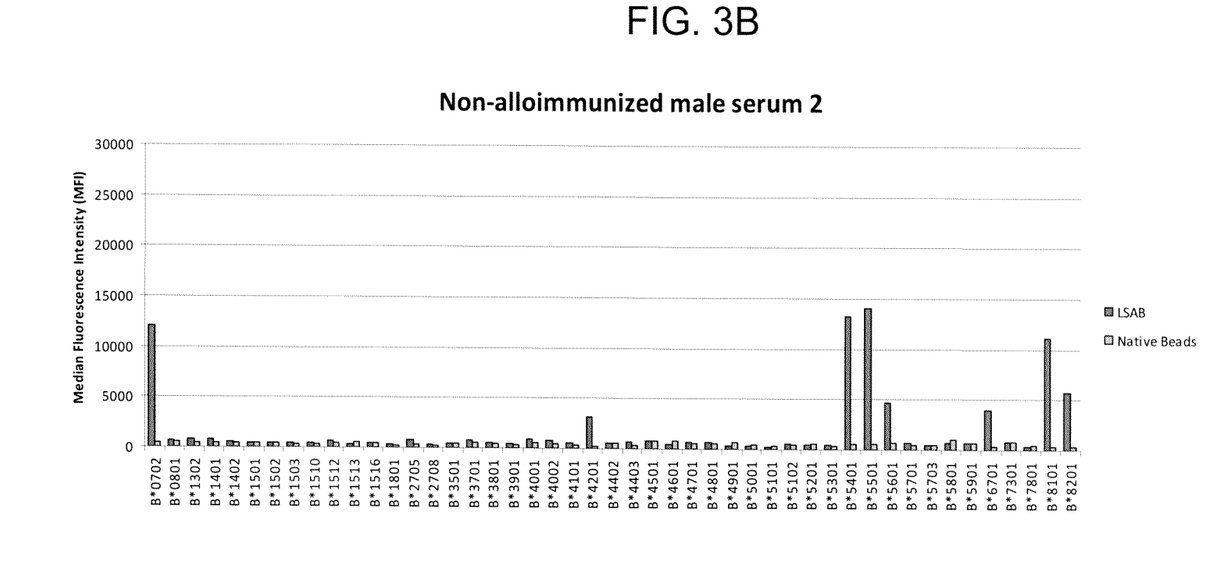
Figure 3C:
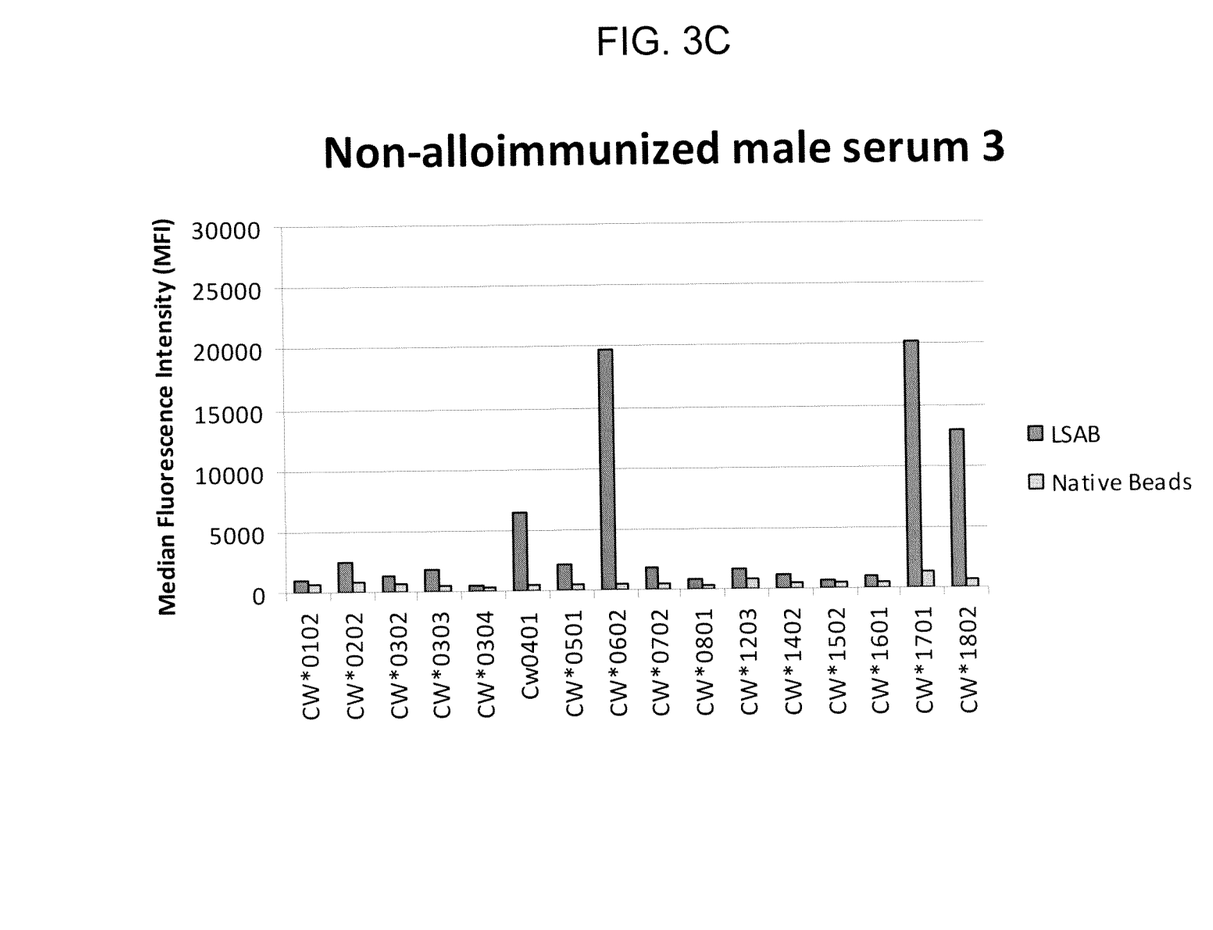

A further investigation was performed comparing the reactivity profile of antibodies in nonalloimmunized male sera to LSAB beads and microbeads prepared in accordance with Example 1. FIGS. 3A-3C show the reactivity of three nonalloimmunized male sera with LSAB and native class I HLA microbeads for A-locus (FIG. 3A), B-locus (FIG. 3B), and C-locus (FIG. 3C) HLA alleles. In all three cases (A-locus, B-locus and C-locus), the results show high positive reactivity of antibodies in the sera with LSAB microbeads but not native class I HLA microbeads. For antibody reactivity to the A-locus alleles tested, there was an average of a 98.3% reduction in MFI when using native class I HLA microbeads compared to LSAB beads. For antibody reactivity to the B-locus alleles tested, there was an average of a 94.3% reduction in MFI when using native class I HLA microbeads compared to LSAB beads. For antibody reactivity to the C-locus alleles tested, there was an average of a 89.9% reduction in MFI when using native class I HLA microbeads compared to LSAB beads. These results indicate that antibody binding is primarily due to denatured class I HLA and not due to native class I HLA. As described above, denatured class I HLA on LSAB beads can provide false positive signals and result in the unnecessary exclusion of potential donors. Thus, these results show that native class I HLA microbeads can provide more accurate detection of class I HLAs.

All references cited herein are incorporated herein by reference in their entireties and for all purposes, to the same extent as if each individual publication or patent or patent application were specifically and individually indicated to be incorporated by reference in its entirety for all purposes. Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed:

1. A method of screening for antibodies that bind native human leukocyte antigens, comprising the steps of: a. contacting a sample with a composition comprising 1) a solid substrate having linked thereto purified human leukocyte antigens (HLA) wherein at least 90% of the purified HLA linked to the solid substrate are native HLA and at most 10% of the purified HLA linked to the solid substrate are denatured HLA and 2) a neutralized enzyme selected from the group consisting of a trypsin-like clan protease, trypsin, chymotrypsin and elastase, and b. detecting binding of an antibody to the solid substrate, wherein binding of an antibody to the solid substrate is indicative of a sample comprising antibodies specific for said native human leukocyte antigens.

2. The method of claim 1, wherein the detecting binding of an antibody is performed using flow cytometry.

3. The method of claim 1, wherein the detecting binding of the antibody is performed using a secondary antibody.

4. The method of claim 3, wherein the secondary antibody comprises a label selected from the group consisting of a radioactive label, a fluorescent label, an enzymatic label, an avidin label a biotin label and combinations thereof.

5. The method of claim 1, wherein the solid substrate comprises a plurality of microbeads or microparticles.

6. The method of claim 5, wherein the solid substrate comprises a plurality of microbeads, wherein each microbead of the plurality comprises a detectable label.

7. The method of claim of claim 6, wherein the detectable label is a fluorescent dye, a radioactive label, a magnetic label, or a bar code.

8. A kit comprising a composition comprising 1) a solid substrate having linked thereto purified human leukocyte antigens (HLA) wherein at least 90% of purified HLA linked to the solid substrate are native HLA and at most 10% purified HLA linked to the solid substrate are denatured HLA and 2) a neutralized enzyme selected from the group consisting of a trypsin-like clan protease, trypsin, chymotrypsin or elastase, and a reagent for detecting the binding of antibody to the solid substrate.

9. The kit of claim 8, wherein the reagent comprises a secondary antibody.

10. The kit of claim 9, wherein the secondary antibody comprises a label selected from the group consisting of a radioactive label, a fluorescent label, an enzymatic label, an avidin label and a biotin label.

* * * * *